United States Patent [19]

Modi

[11] Patent Number: 5,741,482

[45] Date of Patent: Apr. 21, 1998

[54] AIR TREATMENT GEL COMPOSITIONS

[75] Inventor: Jashawant J. Modi, Hockessin, Del.

[73] Assignee: Hercules Incorporated, Wilmington, Del.

[21] Appl. No.: 743,687

[22] Filed: Nov. 6, 1996

[51] Int. Cl.$^6$ .................................................. A61L 9/01
[52] U.S. Cl. .................................. 424/76.3; 424/76.4
[58] Field of Search .................... 523/102; 424/76.3, 424/485

[56] References Cited

U.S. PATENT DOCUMENTS

| | | | |
|---|---|---|---|
| 2,691,615 | 10/1954 | Turner et al. | 167/24 |
| 2,927,055 | 3/1960 | Lanzet | 167/42 |
| 3,956,173 | 5/1976 | Towle | 252/316 |
| 3,969,280 | 7/1976 | Sayce et al. | 252/522 |
| 4,056,612 | 11/1977 | Lin | 424/76 |
| 4,137,196 | 1/1979 | Sakurai et al. | 252/522 |
| 4,318,746 | 3/1982 | Claffey et al. | 106/194 |
| 4,511,552 | 4/1985 | Cox | 424/14 |
| 4,515,909 | 5/1985 | Sawano et al. | 525/102 |
| 4,548,734 | 10/1985 | Chaux et al. | 252/311 |
| 4,755,377 | 7/1988 | Steer | 424/764 |
| 4,842,761 | 6/1989 | Rutherford | 523/102 |
| 5,034,222 | 7/1991 | Kellett et al. | 424/76.4 |
| 5,422,134 | 6/1995 | Hart et al. | 426/573 |
| 5,480,984 | 1/1996 | Angerer et al. | 536/88 |

FOREIGN PATENT DOCUMENTS

| | | |
|---|---|---|
| 49012046 | 2/1974 | Japan . |
| 80001812 | 11/1977 | Japan . |
| 81007434 | 12/1978 | Japan . |
| 81007435 | 4/1979 | Japan . |
| 60135058 A | 7/1985 | Japan . |
| 2103224 | 2/1983 | United Kingdom . |

*Primary Examiner*—Peter F. Kulkosky
*Attorney, Agent, or Firm*—Martin F. Sloan

[57] ABSTRACT

Disclosed are air treatment gel compositions comprising in an aqueous medium, at least one volatile air treatment agent and a polymeric gelling agent consisting essentially of seaweed gum, guar or guar derivatives and, optionally, non-sulfated water-soluble polymer, wherein the bulk density of the composition is greater than about 0.9.

45 Claims, No Drawings

AIR TREATMENT GEL COMPOSITIONS

FIELD OF THE INVENTION

This invention relates to solid air treatment gel compositions.

BACKGROUND OF THE INVENTION

Air treatment gels operate by continuously releasing volatile air treatment components from the gel. The volatile air treatment components can include air freshening ingredients such as disinfectants, bactericides and odoriferous materials which provide a pleasant odor or reduce unpleasant odors, as well as insecticidal materials for insect control.

The air treatment gels generally consist of an aqueous medium containing the volatile air treatment components, and a gelling agent which gels the largely aqueous medium.

U.S. Pat. No. 2,927,055, which is incorporated herein by reference in its entirety, discloses air freshener gel comprising an aqueous medium with about 2.5% of a gelling agent comprising carrageenan, locust bean gum, potassium chloride, a small amount of carboxymethyl cellulose, and a volatile air freshener component.

U.S. Pat. No. 2,691,615, which is incorporated herein by reference in its entirety, relates to air freshener gels comprising an aqueous-alcohol medium with about 4% of a gelling agent comprising agar-agar and a volatile air freshener component.

In U.S. Pat. No. 4,056,612, which is incorporated herein by reference in its entirety, there is disclosed an air freshener gel consisting essentially of a gelling agent comprising carrageenan, locust bean gum, a water-soluble ammonium salt having a pH greater than about 5, and a volatile air freshener component.

U.S. Pat. No. 4,755,377 discloses an aqueous-based air-treating composition comprising a gel base including a gel-forming agent and a gaseous component in an mount effective to provide a bulk density of the composition of about 0.5 to about 0.9 g/cc. The gel-forming agent includes carrageenan, agars, algins and other carbohydrates typically used for such gelled products. Typically the gel base includes a viscosity control agent to reduce the creaming of the air bubbles in the aerated gel. The viscosity control agents include water-soluble cellulose derivatives, e.g., carboxymethyl cellulose, naturally occurring plant extracts such as xanthan, locust bean gum, guar gum, and the mineral-derived thickeners. The viscosity control agents are included at levels up to about 3% of the gel base.

Japanese Patent Application 80001812(80)-B relates to a composition consisting of 92–97 wt. % aqueous medium containing a volatile component for treating air and 3–8% gelling agent consisting of carrageenan, partially saponified polyvinyl acetate, and optionally locust bean gum.

Japanese Patent Application 81007435(81)-B discloses an air treatment gel containing a gelling agent composed of carrageenan, locust bean gum and partially saponified polyvinyl acetate.

The disclosure of Japanese Patent Application 81007434 (81)-B relates to a gel base for a deodorant containing carrageenan and sodium alginate, or carrageenan, sodium alginate and polyvinyl alcohol.

UK Patent No. 2,103,224B discloses gel compositions comprising cellulose surfate, an inorganic metal salt, and at least one other water-soluble polymer. The water-soluble polymer may be a water-soluble cellulose derivative or a natural polysaccharide, e.g., locust bean gum, guar, agar, carrageenan, or xanthan gum.

SUMMARY OF THE INVENTION

This invention relates to novel air treatment gel compositions comprising, in an aqueous medium, at least one volatile air treatment agent and a polymeric gelling agent consisting essentially of seaweed gum and guar or guar derivatives, wherein the bulk density of said composition is greater than about 0.9. It also relates to the gel composition comprising, in an aqueous medium, at least one volatile air treatment agent and a polymeric gelling agent consisting essentially of seaweed gum, guar or guar derivatives and additional non-sulfated water-soluble polymer wherein the bulk density of said composition is greater than about 0.9.

Utilization of guar or guar derivatives in the air treatment gel compositions improves dimensional stability and freeze thaw stability.

DETAILED DESCRIPTION OF THE INVENTION

The seaweed gums for use in the compositions of this invention are those polysaccharides isolated from a number of species of marine algae. They include agar, alginate, carrageenan, fucoidan, furcellaran and laminaran. The preferred seaweed gums are carrageenan, alginate, agar and furcellaran, and the most preferred are carrageenan and agar.

Carrageenan is a sulfated polysaccharide derived from red algae. It is reported to be composed principally of α-D-galactopyranose-4-sulfate units and 3,6-anhydro-α-D-galactopyranose units. At least three forms are known, designated, respectively, as iota, kappa and lambda carrageenan, which differ in the ratios of the two galactopyranose units and accordingly in their sulfate ester content. All three forms are suitable for use in the invention. The kappa and iota carrageenans are preferred, and the kappa is most preferred.

In the context of this invention the term "seaweed gum" also includes commercially available crude carrageenan materials generically known as "alkali-treated seaweed" or ATC. It is also known by various synonyms such as, e.g., processed eucheuma seaweed (PES), seaweed flour, seaweed gum, eucheuma gum, cellugeenan, ATG, and ground seaweed.

Agar is a polysaccharide isolated from various species of red-purple seaweeds, the structure is thought to be predominantly repeating units of alternating β-D-galactopyranosyl and 3,6-anhydro-α-L-galactopyranosyl units coupled 1→3.

The principal source of algin, or alginate, is the giant kelp *Macrocystis pyrifera*. The structure is considered to be a linear polymer consisting exclusively of β-D-(1→4)-linked mannuronic acid units and α-L-(1→4)-linked guluronic acid units. The most common form of algin is sodium alginate.

Furcellaran is an extract of the red alga *Furcellaria fastigiata*. It consists mainly of units of D-galactose, 3,6-anhydro-D-galactose, and the half-ester sulfate of these sugars. The structure of furcellaran is very much like that of kappa-carrageenan, the main difference being that furcellaran contains about one sulfate group per three to four monomer units, while kappa-carrageenan contains about one sulfate group per two monomer units.

The other gum ingredient required for use in the invention is guar or derivatives of guar. Guar is preferred. Guar is derived from the seed of the guar plant. It consists of linear chains of (1→4)-β-D-mannopyranosyl units with α-D-galaetopyranosyl units attached by (1→6) linkages. The ratio of D-galactose to D-mannose in guar is 1:2.

The derivatives of guar that may be used in the compositions of the invention include carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMCP guar), hydrophobically modified cationic guar (HM cationic guar), and mixtures thereof.

In the air treatment gel compositions of the invention the minimum level of seaweed gum plus guar or guar derivatives preferably is about 0.5% based on the total weight of the composition. A more preferable minimum level is about 0.75%, and the most preferable level about 1%. The preferred maximum level is about 25%, a more preferred maximum about 15%, and the most preferred maximum about 5%.

The minimum level of seaweed gum in the compositions is preferably about 0.5% based on the total weight of the composition, and a more preferred minimum level about 1%. The preferred maximum level is about 25%, a more preferred maximum about 10%, and the most preferred maximum about 5%.

The minimum level of guar or guar derivatives in the compositions is preferably about 0.1% based on the total weight of the composition, more preferably about 0.5% and most preferably about 1%. The preferred maximum level is about 25%, a more preferred maximum about 10%, and the most preferred maximum about 5%.

The air treatment gel compositions of this invention may include, in addition to seaweed gum and guar or guar derivatives, additional non-sulfated water-soluble polymers. These include, but are not restricted to, locust bean gum, xanthan, scleroglucan, dextran, pectin, pectin derivatives, gum ghatti, gum arabic, gum karaya, cellulose ethers, starch, starch derivatives, gelatin, casein, gellan gum, polyethylene glycols or derivatives thereof with average molecular weight of about 500 or higher, acrylic acid polymers, polyvinyl alcohol, and mixtures thereof. Preferred non-sulfated water-soluble polymers are locust bean gum and cellulose ethers.

Non-sulfated water-soluble cellulose ethers suitable for use in the invention include hydroxyethyl cellulose (HEC), hydroxypropyl cellulose (HPC), water-soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC), cationic hydrophobically modified hydroxyethyl cellulose (cationic HMHEC), and mixtures thereof. The preferred water-soluble cellulose ethers are carboxymethylcellulose and hydroxyethyl cellulose.

When additional non-sulfated water-soluble polymer is utilized in the compositions of this invention, it will preferably be used at a level of from about 0.1% to about 20% on a weight basis based on the total weight of the composition. More preferably it will be used at a level of from about 0.5% to about 10%, and most preferably from about 1% to about 5% based on the total weight of the composition.

The air freshener compositions of this invention include volatile air treatment agents such as insect control agents or air freshener ingredients, or both. Preferably these components are volatile materials at room temperature, compatible with the other ingredients in the gel, and dispersible in aqueous medium. The volatile air treatment agents include disinfectants, bactericides, fungicides, deodorants, pest repellants, insecticides, odoriferous materials and mixtures thereof. Odoriferous materials useful for reducing unpleasant odors include oil of rose, oil of lime, oil of lemon, oil of spearmint, oil of wintergreen, oil of cedar wood, oil of fir Canadian, and the like. These oils may also be used in combination with fragrances such as aromatic esters, aldehydes, ketones, and other compounds known to those skilled in the art of blending fragrances.

Other optional ingredients for use in the novel gel compositions of this invention are water-soluble inorganic salts, which are used to promote gelling of the compositions. Operable salts include those of potassium, sodium, calcium, magnesium, aluminum and ammonium. Generally the salts are chlorides, sulfates, phosphates, acetates or carbonates.

Examples of salts for use in the invention are potassium chloride, sodium chloride, calcium chloride, aluminum acetate, aluminum sulfate and dihydroxy aluminum sodium carbonate. Preferred salts are potassium chloride, sodium chloride and ammonium chloride. The most preferred is potassium chloride. When used, the optimum amount of salt is variable and will depend on the particular salt chosen and particular mixture of gums employed. The amount of salt may be adjusted to obtain particularly desirable properties in the product gels. Generally they will be used at levels of from about 0.1% to about 5% based on the total weight of the composition.

It is often desirable to include in the gel formulations antifreeze and/or humectant ingredients. The preferred materials for this purpose are polyols, i.e., alcohols containing more than one hydroxyl group. Polyols useful for this purpose include, but are not restricted to, glycerol, propylene glycol, polyethylene glycol, sorbitol, inositol, mannitol, galactidol, arabitol, ribitol, xylitol and mixtures thereof. Antifreeze or humectant ingredients are preferably utilized at levels of from about 0.1% to about 25% based on the total weight of the composition. More preferably they are used at from about 1% to about 10% and most preferably from about 1% to about 5%.

Mineral or organic acids may also be included in the gel compositions of this invention. The acids serve to increase the rate of gelation by lowering pH. Examples of organic acids which are commonly used for this application are citric acid, formic acid fumaric acid, benzoic acid, acetic acid, oxalic acid, adipic acid, salicylic acid, phthalic acid, sebacic acid, palmitic acid, stearic acid, phenylstearic acid and oleic acid. Any of the common mineral acids such as hydrochloric acid and sulfuric acid may also be utilized. When they are used, the acids are preferably present at levels not exceeding about 1 wt. % based on the total weight of the composition.

Other ingredients which may be present in the gel compositions of this invention, in addition to those already mentioned, include surfactants or emulsifiers, preferably anionic or non-ionic, well known in the art. Exemplary of the types of anionics are the alkyl sulfonates, alkyl sulfates or alkyl ether sulfates. Examples of classes of non-ionic surfactants or emulsifiers are polyethoxylate ethers, sorbitan esters and polyethoxylates of sorbitan esters.

Also, the compositions may contain preservatives, i.e., bactericides or fungicides to inhibit microbial or fungal growth in the air treatment gel. Typically they are present at levels of from about 0.001% to about 2%, preferably from about 0.001% to about 0.5%. Any of the common bactericides or fungicides well known in the are may be used. Examples are sodium benzoate, and methyl-, butyl- or propyl-p-hydroxybenzoate.

The air treatment gel composition may also contain dyes which impart color to the gel. Generally they am used at levels up to about 0.05%.

The air treatment gel compositions of the contain water-insoluble materials such as clays, organosoluble clays such as hydrogenated tallow benzylammonium hectorite, hydrophobic silicas and wax, as well as additional water-soluble materials such as hydrophobic silicas and alkali metal salts of $C_{12}$–$C_{20}$ carboxylic acids, e.g., sodium stearate.

In addition, the aqueous medium of the air treatment gel can contain carrier agents which provide increased solubility for the particular oils, fragrances and insecticidal ingredients used. They may be present in the gel in the range of from about 1% to about 10%. Typically, the carrier agents are water miscible solvents in which the oils, fragrances and insecticidal ingredients are at least partially soluble. Examples of such materials are isopropanol, ethylene glycol, glycerol, propylene glycol, hexylene glycol, cellosolve, or the like.

The air treatment gel compositions of the present invention are typically prepared as follows. The seaweed gum, guar or guar derivatives and additional non-sulfated water-soluble polymer (if utilized) are blended and then dispersed in water. Solution is effected by stirring and heating at a temperature between about 60° C. and 90° C. until the polymers are completely dissolved. The solution is then cooled to about 60° C., and the other ingredients are added. Further cooling to approximately room temperature provides the air treatment gel composition. Before gelation the solution typically will be poured into a suitable container or mold so as to provide a gel having the desired shape.

The product gel compositions of the invention are sufficiently rigid to be generally free-standing, yet are sufficiently flexible to resist crumbling or breaking. They exhibit low syneresis, i.e., separation of liquid from the gel, high gel strength, and good freeze/thaw and storage stability. They generally have sufficient strength so that they will not sag but will be maintained in the container so that air can easily and freely contact the surface to transfer the volatile ingredients to the surrounding room or space. If desired, gels with lower rigidity can be prepared by reducing the level of the polymeric gelling agent.

This invention is illustrated by the following examples, which are exemplary only and not intended to be limiting. All percentages, parts, etc., are by weight, unless otherwise indicated.

Materials

Carrageenan: Genugel® CHP-1 (predominantly kappa carrageenan), Genugel® CHP-2 (predominantly kappa carrageenan standardized with salt), and Genugel® RLV (kappa/lambda carrageenan standardized with salt and sugar) from Hercules Incorporated, Wilmington, Del.

Agar: Algamar Agar Agar MZA 100, type 900 from Algas Marinas, Santiago, Chile.

Processed Eucheuma Seaweed (PES) from Hercules Incorporated, Wilmington, Del.

Guar: Supercol® K-1 (viscosity of 600–1,500 cps as 1% aqueous solution) and Supercol® U (viscosity of 4,500–5,500 cps as 1% aqueous solution) from Hercules Incorporated, Wilmington, Del.

Hydroxypropyl guar (HP guar): Galactosol® 40H4FD 1 from Hercules Incorporated, Wilmington, Del.

Hydrophobically modified hydroxyethyl cellulose (HMHEC): Natrosol® Plus 330 from Hercules Incorporated, Wilmington, Del.

Carboxymethyl Cellulose 7LT (viscosity, 25–50 cps, 2% aqueous solution), Carboxymethyl Cellulose 9M8F (viscosity, 400–800 cps, 2% aqueous solution, DS 0.8–0.95), and Carboxymethyl Cellulose 7MF (viscosity, 400–800 cps, 2% aqueous solution, DS 0.65–0.9), from Hercules Incorporated, Wilmington, Del.

Locust bean gum: Genu Gum® RL200Z from Hercules Incorporated, Wilmington, Del.

Carboxymethyl Guar: Carboxymethyl Guar GPX 230 (viscosity, 3,000–4,000 cps, 1 % aqueous solution) from Hercules Incorporated, Wilmington, Del.

Low Viscosity Carboxymethyl Guar (LVCM Guar) was prepared by the method described in U.S. Pat. No. 5,480,984 to Angerer et al., which is incorporated herein in its entirety by reference.

Cationic guar: Guar hydroxypropyl trimethyl ammonium chloride, N-Hance® 3000, from Hercules Incorporated, Wilmington, Del.

Preservative: Germaben® II from Sutton Laboratories, Chatham, N.J.

Anionic surfactant: Dowfax® 2A1 from Dow Chemical Co., Midland, Mich.

Non-ionic surfactant: Triton® X100 from Rohm & Haas, Philadelphia, Pa.

Fragrance: from Flavor and Fragrance Specialties, Franklin Lakes, N.J.

Insect repellent: Insect Repellent Lot #32948, from Flavor and Fragrance Specialties, Franklin Lakes, N.J.

Starch: Thermoflo® from National Starch and Chemical Co., Bridgewater, N.J.

EXAMPLES 1–24 AND COMPARATIVE EXAMPLES A–E

The procedure for preparing the gel compositions of these examples was as follows. Water was heated and stirred at 90° C. The polymers and inorganic salts were dry blended and then sifted into the vortex of the stirred water. Mixing was continued for 20 minutes at 90° C., and then the solution was cooled to about 75° C. At this point any other ingredients exclusive of fragrance and dye were added followed by mixing for 5 minutes. Then the flagrance and dye were added followed by mixing for 5 minutes. The resulting mixture was dispensed into a plastic jar and allowed to cool.

Gel strength is the amount of force (in grams) required for a 1.27 cm diameter probe to press the gel by 2 mm. The test was run on a Voland-LFRA Texture Analyzer. The results reported are the average of three determinations. Samples were aged at room temperature for at least 24 hours before testing.

For the dimensional stability test an approximately 40 mm high×40 mm diameter gel sample as place in a 100 mm high×50 mm diameter glass jar. The jar was capped and the sample was placed in an oven at 51° C. The change in dimension of the gel at 51° C. was determined after 1 and 4 weeks. The values are presented as percent of the original dimensions.

For the freeze/thaw test a hot solution of air treatment gel was poured into a 118.3 ml glass jar. The uncapped sample jar was allowed to cool to room temperature for 2 hours, and then the jar was capped and allowed to stand overnight at room temperature. The capped jar was then place in a −5° C. freezer for 20 hours and then removed and kept at room temperature for 20 hours. The sample was then tested for gel strength as above. The values in the tables are the average of 3 measurements.

Results are presented in Tables 1, 2, 3 and 4. For comparison, the gel strength of two commercially available cone shaped air fresheners was determined. These were Renuzit® Longlast Adjustable Air Fresheners: (a) Bath & Boutique, and (b) Nature's Orchard. The gel strength of (a) was determined to be 127 g at top, 173 g at the side and 78 g at the bottom. The gel strength of (b) was determined to be 135 g at top, 175 g at the side and 89 g at the bottom.

The results in Tables 1–4 indicate that the compositions of this invention have gel strengths at least as high as those exhibited by commercially available air fresheners.

Comparative Examples A–E all lack guar or guar derivatives. The compositions of Example A exhibit poor dimensional stability, and those of Examples B–E exhibit inferior freeze thaw stability when compared to compositions of the invention.

TABLE 1

| Ingredient | Example 1 | Example 2 | Example 3 | Example 4 | Example 5 |
|---|---|---|---|---|---|
| Genugel CHP-1 carrageenan | 2.70 | 2.70 | 1.35 | 2.70 | — |
| Genugel CHP-2 carrageenan | — | — | — | — | 1.80 |
| Supercol K-1 guar | 0.30 | 0.30 | 0.15 | 0.30 | 1.20 |
| Natrosol Plus 330 HMHEC | — | 0.03 | 0.02 | 0.06 | — |
| Potassium chloride | 1.00 | 1.00 | 1.00 | 1.00 | 0.60 |
| Germaben II Preservative | 1.00 | 1.00 | 1.00 | — | 1.00 |
| Fragrance | 3.00 | 3.00 | 3.00 | 3.00 | 1.00 |
| Water | 92.00 | 91.97 | 93.48 | 92.94 | 94.40 |
| Gel Strength (g) | 778 | 786 | 310 | ND | 284 |
| Bulk Density (g/ml) | 0.99 | 1.00 | 1.00 | 1.00 | ND |

ND = Not determined

TABLE 2

| Ingredient | Example 6 | Example 7 | Example 8 | Example 9 | Example 10 | Example 11 | Example 12 | Example 13 |
|---|---|---|---|---|---|---|---|---|
| Genugel RLV carrageenan | 2.70 | 1.13 | 1.13 | 1.50 | 2.25 | 1.80 | 1.80 | 1.50 |
| Supercol K-1 guar | 0.30 | — | — | 1.50 | 0.75 | 1.20 | 1.20 | — |
| Supercol U guar | — | 0.37 | — | — | — | — | — | 1.50 |
| Galactosol 40H4FD1 HP guar | — | — | 0.37 | — | — | — | — | — |
| Natrosol Plus 330 HMHEC | 0.03 | 0.03 | 0.03 | — | — | — | 0.06 | 0.06 |
| Potassium chloride | 1.00 | 1.13 | — | — | — | — | — | — |
| Germaben II preservative | 1.00 | 1.00 | 1.00 | 1.00 | 1.00 | — | — | — |
| Fragrance | 3.00 | 30.00 | 30.00 | 3.00 | 3.00 | 3.00 | 3.00 | 3.00 |
| Dowfax 2A1 surfactant | — | 0.50 | 0.50 | — | — | — | — | — |
| Water | 91.97 | 65.84 | 66.97 | 93.00 | 93.00 | 94.00 | 93.94 | 93.94 |
| Gel strength (g) | 408 | ND | ND | 108 | 193 | 142 | 168 | 95 |
| Bulk Density (g/ml) | ND | ND | ND | 0.99 | 1.00 | ND | ND | ND |

TABLE 3

| Ingredient | Example 14 | Example 15 | Example 16 | Example 17 | Example 18 |
|---|---|---|---|---|---|
| Agar | 1.50 | 0.75 | 1.50 | 1.125 | 0.75 |
| Supercol K-1 guar | 0.50 | 0.25 | 0.50 | 0.375 | 0.25 |
| Natrosol Plus 330 HMHEC | — | — | 0.02 | 0.015 | 0.02 |
| Germaben II preservative | — | — | 1.00 | 1.00 | — |
| Fragrance | 3.00 | 3.00 | 3.00 | 3.00 | 3.00 |
| Water | 95.00 | 96.00 | 93.98 | 94.485 | 95.98 |

TABLE 3-continued

| | Air Treatment Gel Compositions (parts/hundred) | | | | |
|---|---|---|---|---|---|
| Ingredient | Example 14 | Example 15 | Example 16 | Example 17 | Example 18 |
| Gel strength (g) | 299 | 108 | 236 | 187 | 95 |
| Bulk Density (g/ml) | ND | ND | ND | 1.00 | 1.00 |

TABLE 4

| | Air Treatment Gel compositions (parts/hundred) | | | | | | | | | | |
|---|---|---|---|---|---|---|---|---|---|---|---|
| Ingredient | Exp. 19 | Comp. Exp. A | Exp. 20 | Exp. 21 | Exp. 22 | Comp. Exp. B | Exp. 23 | Comp. Exp. C | Exp. 24 | Comp. Exp. D | Comp. Exp. E |
| Genugel CHP-1 carrageenan | 2.00 | 3.00 | 2.00 | — | — | — | 1.20 | 1.20 | 1.80 | 3.00 | 1.80 |
| Genugel CHP-2 carrageenan | — | — | — | — | 1.80 | 1.80 | — | — | — | — | — |
| CMC 7LT | — | — | — | — | — | 1.20 | — | 0.80 | — | — | 1.20 |
| Supercol K-1 guar | 0.50 | — | 0.50 | 0.25 | 1.20 | — | 0.80 | — | 1.20 | — | — |
| Agar | — | — | — | 0.75 | — | — | — | — | — | — | — |
| KCl | 0.63 | — | 0.63 | 0.10 | 0.60 | 0.60 | 0.80 | 0.80 | 1.20 | 1.20 | 1.20 |
| Germaben II | 1.00 | 1.00 | 1.00 | 1.00 | 1.00 | 1.00 | 1.00 | 1.00 | 1.00 | 1.00 | 1.00 |
| Fragrance | 1.00 | 1.00 | 1.00 | 1.00 | 1.00 | 1.00 | 1.00 | 1.00 | 1.00 | 1.00 | 1.00 |
| Triton X-100 | — | — | 0.50 | 0.50 | — | — | — | — | — | — | — |
| Propylene Glycol | — | — | 5.00 | 5.00 | — | — | — | — | — | — | — |
| Water | 94.88 | 95.00 | 89.38 | 91.40 | 94.40 | 94.40 | 95.20 | 95.20 | 93.80 | 93.80 | 93.80 |
| Gel Strength (g) | 522 | 210 | 488 | 90 | 300 | 400 | 260 | 270 | 460 | 800 | 520 |
| Freeze/Thaw, 3 cycles, Gel Strength (g) | ND | 300 | ND | ND | 320 | 240 | 260 | 160 | 410 | 300 | 250 |
| Dimensional Stability at 51° C., % | ND | 78 | ND | ND | 100 | 100 | 97 | 100 | 100 | ND | 100 |

EXAMPLES 25–39 AND COMPARATIVE EXAMPLES F AND G

The procedure for preparing the gel compositions of these examples was as follows. Water was heated and stirred at 85–90° C. The carrageenans, guar, carboxymethyl guar, carboxymethyl cellulose, agar, locust bean gum, and potassium chloride were dry blended and then sifted into the vortex of the stirred water. Mixing was continued for 20 minutes, and then the solution was cooled to about 80° C. At this point a slurry of aluminum acetate, basic (when used) and cationic guar (when used) in 10g of water was added, and the resulting mixture was mixed for about 10 minutes. A solution of aluminum acetate (when used), basic berated, aluminum acetate (when used) and citric acid (when used) in 10 g of water was then added followed by mixing for 10 minutes. The remaining ingredients were then added followed by mixing for 10 minutes, and then the compositions were poured into jars for cooling and storage.

Evaluation of the gels was carded out as described above. The results are presented in Tables 5 and 6.

In Comparative Examples F and G, where guar but not seaweed gum was utilized, only very low gel strength levels were obtained.

TABLE 5

| | Air Treatment Gel compositions (parts/hundred) | | | | | | |
|---|---|---|---|---|---|---|---|
| Ingredients | Example 25 | Example 26 | Example 27 | Example 28 | Example 29 | Example 30 | Example 31 |
| Processed Eucheuma Seaweed | — | — | — | 1.80 | — | — | — |
| Genugel CHP-1 carrageenan | 1.00 | — | 1.80 | — | 1.20 | 1.20 | 1.20 |
| Supercol K-1 guar | 0.50 | 0.37 | — | 1.20 | 1.20 | 1.20 | 0.60 |
| Agar | — | 0.60 | — | — | — | — | — |
| Genu Gum RL200Z locust bean gum | 0.60 | — | 0.60 | 0.75 | — | — | — |
| KCl | | | | | | | |
| Aluminium acetate, basic pure | — | — | — | — | 0.10 | — | — |
| Aluminum acetate, basic borated | — | — | — | — | — | — | 0.10 |
| Aluminum sulfate 18H$_2$O | — | — | — | — | — | 0.33 | — |
| Citric acid | — | — | — | — | — | 0.08 | — |
| Carboxymethyl guar GPX230 | — | 0.37 | — | — | — | — | — |
| CMC 9M8F | 1.50 | — | — | — | — | — | — |
| CMC 7MF | — | — | — | — | 1.00 | 1.00 | 1.00 |
| Low Viscosity Carboxymethyl Guar (36% solids) | — | 1.47 | — | — | — | — | — |
| Cationic guar N-Hance ® 3000 | 0.50 | — | 1.20 | — | — | — | — |
| Germaben II | 1.00 | 1.00 | 1.00 | 1.00 | — | — | — |

TABLE 5-continued

Air Treatment Gel compositions (parts/hundred)

| Ingredients | Example 25 | Example 26 | Example 27 | Example 28 | Example 29 | Example 30 | Example 31 |
|---|---|---|---|---|---|---|---|
| Fragrance | 1.00 | 1.00 | 1.00 | 1.00 | 1.00 | 1.00 | 1.00 |
| Glycerol | — | — | — | — | — | — | 1.00 |
| Dye | 3–4 drops | 3–4 drops | 3–4 drops | 3–4 drops | 3–4 drops | 3–4 drops | 3–4 drops |
| Water | 93.90 | 95.04 | 94.40 | 94.25 | 95.50 | 95.19 | 95.10 |
| Gel Strength (g) | 102 | 59 | 256 | 351 | 52 | 160 | 48 |
| Bulk Density (g/ml) | 1.01 | 0.99 | 1.00 | 0.99 | 1.00 | 0.99 | 0.99 |

TABLE 6

Air Treatment Gel compositions (parts/hundred)

| Ingredients | Exp. 32 | Exp. 33 | Exp. 34 | Exp. 35 | Exp. 36 | Exp. 37 | Exp. 38 | Exp. 39 | Comp. Exp. F | Comp. Exp. G |
|---|---|---|---|---|---|---|---|---|---|---|
| Genugel CHP-1 carrageenan | 1.8 | 1.80 | 1.80 | 0.90 | 0.90 | 1.80 | 1.80 | 1.80 | — | — |
| Supercol K-1 guar | 1.2 | 1.20 | 0.60 | 0.60 | 0.60 | — | 0.60 | — | 1.20 | 1.20 |
| CMC 7LT | — | — | 0.60 | 0.60 | 0.60 | — | — | — | — | — |
| Agar | — | — | — | 0.90 | — | — | — | — | — | — |
| Genu Gum RL200Z locust bean gum | — | — | — | — | 0.90 | — | — | — | 1.8 | 1.8 |
| KCl | 0.60 | 0.60 | 0.60 | 0.60 | 0.60 | 0.60 | — | — | — | 0.60 |
| Thermflo | — | — | — | — | — | — | 0.60 | 0.60 | — | — |
| Carboxymethyl Guar GPX 230 | — | — | — | — | — | — | — | 1.20 | — | — |
| Low Viscosity Carboxymethyl Guar (36.0% solids) | — | — | — | — | — | 83.30 | — | — | — | — |
| Germaben II | 1.00 | 1.00 | 1.00 | 1.00 | 1.00 | 1.00 | 1.00 | 1.00 | 1.00 | 1.00 |
| Fragrance | — | 1.00 | 1.00 | 1.00 | 1.00 | 1.00 | 1.00 | 1.00 | 1.00 | — |
| Insect Repellent | 1.00 | — | — | 1.00 | 1.00 | — | — | — | 1.00 | — |
| Dye | 3–4 drops | 3–4 drops | 3–4 drops | 3–4 drops | 3–4 drops | 34 drops | 3–4 drops | 3–4 drops | 3–4 drops | 34 drops |
| Distilled water | 94.40 | 94.40 | 94.40 | 94.40 | 94.40 | 12.30 | 94.40 | 94.40 | 95.00 | 94.40 |
| Gel Strength (g) | 383 | 405 | 432 | 215 | 305 | 105 | 295 | 515 | 7 | 7 |
| Bulk Density (g/ml) | 0.99 | 0.99 | 0.99 | 0.99 | 0.99 | 0.99 | 0.99 | 0.98 | 0.99 | 0.99 |

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. An air treatment gel composition comprising in an aqueous medium, at least one volatile air treatment agent and a polymeric gelling agent consisting essentially of a) seaweed gum, b) guar or guar derivatives and c) additional non-sulfated water-soluble polymer selected from the group consisting of locust bean gum, hydroxyethyl cellulose (HEC), water-soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMFEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC), cationic hydrophobically modified hydroxyethyl cellulose (cationic HMHEC), and mixtures thereof, wherein the bulk density of said composition is greater than about 0.9, the seaweed gum is from about 0.5% to about 25% of the total weight of the composition, the guar or guar derivatives is from about 0.1% to about 25% of the total weight of the composition, and the additional non-sulfated water-soluble polymer is from about 0.1% to about 20% of the total weight of the composition; and wherein the air freshener composition has freeze-thaw resistance greater than a composition that is the same except that it contains no guar or guar derivative.

2. The composition of claim 1 wherein the bulk density is greater than about 0.95.

3. The composition of claim 2 wherein the bulk density is greater than about 0.98.

4. The composition of claim 1 wherein the seaweed gum is selected from the group consisting of carrageenan, alkali-treated seaweed, agar, alginate, furcellaran and mixtures thereof.

5. The composition of claim 1 further comprising water-soluble inorganic salt.

6. The composition of claim 5 where the water-soluble inorganic salt is selected from the group consisting of salts of potassium, sodium, calcium, magnesium, aluminum and ammonium.

7. The composition of claim 5 where the water-soluble inorganic salt is selected from the group consisting of salts of chloride, sulfate, carbonate and phosphate.

8. The composition of claim 5 where the water-soluble inorganic salt is selected from the group consisting of potassium chloride, sodium chloride, calcium chloride, aluminum acetate, aluminum sulfate and dihydroxy aluminum sodium carbonate.

9. The composition of claim 1 further comprising polyol selected from the group consisting of glycerol propylene glycol, polyethylene glycol, sorbitol, inositol, mannitol, galactidol, arabitol, ribitol, xylitol and mixtures thereof.

10. The composition of claim 1 wherein the gelling agent is from about 0.5% to about 25% of the total weight of the composition.

11. The composition of claim 10 wherein the gelling agent is from about 0.75% to about 15% of the total weight of the composition.

12. The composition of claim 11 wherein the gelling agent is from about 1% to about 5% of the total weight of the composition.

13. The composition of claim 1 wherein the seaweed gum is from about 1% to about 10% of the total weight of the composition.

14. The composition of claim 1 wherein the seaweed gum is from about 1% to about 5% of the total weight of the composition.

15. The composition of claim 1 wherein the guar or guar derivatives is from about 0.5% to about 10% of the total weight of the composition.

16. The composition of claim 1 wherein the guar or guar derivatives is from about 1% to about 5% of the total weight of the composition.

17. The composition of claim 1 wherein the additional non-sulfated water-soluble polymer is from about 0.5% to about 10% of the total weight of the composition.

18. The composition of claim 17 wherein the additional non-sulfated water-soluble polymer is from about 1% to about 5% of the total weight of the composition.

19. The composition of claim 1 wherein the guar derivatives are selected from the group consisting of carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar), hydrophobically modified cationic guar (HM cationic guar), and mixtures thereof.

20. The composition of claim 1 wherein the volatile air treatment agent is at least one material selected from the group consisting of disinfectants, bactericides, fungicides, deodorants, pest repellants, insecticides, odoriferous materials and mixtures thereof.

21. The composition of claim 1 wherein the additional non-sulfated water-soluble polymer is carboxymethyl cellulose (CMC).

22. The composition of claim 1 wherein the additional non-sulfated water-soluble polymer is hydroxyethyl cellulose (HEC).

23. The composition of claim 1 wherein the additional non-sulfated water-soluble polymer is locust bean gum.

24. The composition of claim 1 wherein the seaweed gum is carrageenan, the guar or guar derivative is guar, the additional non-sulfated water-soluble polymer is selected from the group consisting of CMC, HEC and mixtures thereof, and the gelling agent is from about 0.5% to about 25% of the total weight of the composition.

25. The composition of claim 1 wherein the seaweed gum is agar, the guar or guar derivative is guar, the additional non-sulfated water-soluble polymer is selected from the group consisting of CMC, HEC and mixtures thereof, and the gelling agent is from about 0.5% to about 25% of the total weight of the composition.

26. An air treatment gel composition comprising in an aqueous medium, at least one volatile air treatment agent and a polymeric gelling agent consisting essentially of seaweed gum, and guar or guar derivatives, wherein the bulk density of said composition is greater than about 0.9, the seaweed gum is from about 0.5% to about 25% of the total weight of the composition, the guar or guar derivatives is from about 0.1% to about 25% of the total weight of the composition; and
wherein the air freshener composition has freeze-thaw resistance greater than a composition that is the same except that it contains no guar or guar derivative.

27. The composition of claim 26 wherein the bulk density is greater than about 0.95.

28. The composition of claim 27 wherein the bulk density is greater than about 0.98.

29. The composition of claim 26 wherein the seaweed gum is selected from the group consisting of carrageenan, alkali-treated seaweed, agar, alginate, furcellaran and mixtures thereof.

30. The composition of claim 26 further comprising water-soluble inorganic salt.

31. The composition of claim 30 where the water-soluble inorganic salt is selected from the group consisting of salts of potassium, sodium, calcium, magnesium, aluminum and ammonium.

32. The composition of claim 30 where the water-soluble inorganic salt is selected from the group consisting of salts of chloride, sulfate, carbonate and phosphate.

33. The composition of claim 30 where the water-soluble inorganic salt is selected from the group consisting of potassium chloride, sodium chloride, calcium chloride, aluminum acetate, aluminum sulfate and dihydroxy aluminum sodium carbonate.

34. The composition of claim 26, further comprising polyol selected from the group consisting of glycerol, propylene glycol, polyethylene glycol, sorbitol, inositol, mannitol, galactidol, arabitol, ribitol, xylitol and mixtures thereof.

35. The composition of claim 26 wherein the gelling agent is from about 0.5% to about 25% of the total weight of the composition.

36. The composition of claim 35 wherein the gelling agent is from about 0.75% to about 15% of the total weight of the composition.

37. The composition of claim 36 wherein the gelling agent is from about 1% to about 5% of the total weight of the composition.

38. The composition of claim 26 wherein the seaweed gum is from about 1% to about 10% of the total weight of the composition.

39. The composition of claim 38 wherein the seaweed gum is from about 1% to about 5% of the total weight of the composition.

40. The composition of claim 26 wherein the guar or guar derivatives is from about 0.5% to about 10% of the total weight of the composition.

41. The composition of claim 26 wherein the guar or guar derivatives is from about 1% to about 5% of the total weight of the composition.

42. The composition of claim 26 wherein the guar derivatives are selected from the group consisting of carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar), hydrophobically modified cationic guar (HM cationic guar), and mixtures thereof.

43. The composition of claim 26 wherein the volatile air treatment agent is at least one material selected from the group consisting of disinfectants, bactericides, fungicides, deodorants, pest repellants, insecticides, odoriferous materials and mixtures thereof.

44. The composition of claim 26 wherein the seaweed gum is carrageenan, the guar or guar derivative is guar, and the gelling agent is from about 0.5% to about 25% of the total weight of the composition.

45. The composition of claim 26 wherein the seaweed gum is agar, the guar or guar derivative is guar, and the gelling agent is from about 0.5% to about 25% of the total weight of the composition.

* * * * *